(12) United States Patent
Kayar et al.

(10) Patent No.: US 6,328,959 B1
(45) Date of Patent: Dec. 11, 2001

(54) INTESTINAL HYDROGEN REMOVAL USING HYDROGEN-METABOLIZING MICROBES

(75) Inventors: Susan R. Kayar, Gaithersburg, MD (US); Meyer J. Wolin, Delmar; Terry L. Miller, Slingerlands, both of NY (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/223,315

(22) Filed: Dec. 30, 1998

Related U.S. Application Data

(60) Provisional application No. 60/101,001, filed on Sep. 18, 1998.

(51) Int. Cl.[7] ..................................................... C12N 1/20
(52) U.S. Cl. .......................................... 424/93.4; 424/93.3
(58) Field of Search ................................. 424/93.3, 93.4; 128/200.24

(56) References Cited

U.S. PATENT DOCUMENTS

| | | | |
|---|---|---|---|
| 5,443,826 | * | 8/1995 | Borody ................................ 424/93.3 |
| 5,630,410 | * | 5/1997 | Kayar et al. .................... 128/200.24 |

* cited by examiner

*Primary Examiner*—Jean C. Witz
(74) *Attorney, Agent, or Firm*—Charles H. Harris; Joseph K. Hemby, Jr.

(57) ABSTRACT

Some people suffer from pains in the abdomen that are due to excessive $H_2$ gas produced in the intestine. In this invention, microbes that metabolize $H_2$ are introduced into the intestine in order to accelerate the removal of the $H_2$. The microbes are selected from species that are native to the large intestine of humans or other mammals, and are non-toxic. The end products are either non-gaseous, or significantly smaller volumes of gas than the original $H_2$. The delivery of the microbes is accomplished by any one of several means, with packaging of the microbes in enteric coatings for oral ingestion as a preferred means.

7 Claims, 2 Drawing Sheets

INTESTINAL HYDROGEN REMOVAL USING HYDROGEN-METABOLIZING MICROBES

This application claims the benefit of U.S. Provisional Application 60/101,001, filed Sep. 18, 1998.

BACKGROUND OF THE INVENTION

1. Related Applications

This work is an extension of work previously described in U.S. Pat. No. 5,630,410, in which $H_2$-metabolizing microbes were introduced into the intestines of rats breathing $H_2$ in a hyperbaric chamber. The purpose of the previous invention was to remove some of the $H_2$ dissolved in the tissues of the rats in order to reduce their risk of decompression sickness following the exposure to an atmosphere containing high pressures of $H_2$. The compositions of this invention are related to the compositions of co-pending application Ser. No. 08/852,207, which application, in turn, is a division of U.S. Pat. No. 5,630,410.

2. Field of the Invention

This invention relates to a method for relieving abdominal pains under normal atmospheric conditions caused by hydrogen ($H_2$) gas trapped in the large intestine. More particularly, this invention relates to a process of treating symptoms of irritable bowel syndrome or spastic colon or excessive flatulence or other gastrointestinal distress by assisting in the removal of $H_2$ trapped in the large intestine. This assistance is accomplished by supplying the intestine with an artificial excess amount of microbes that metabolize $H_2$, converting some of the $H_2$ to water and other substances. This product and method supplement and accelerate the removal of $H_2$ from the large intestine that occurs spontaneously with normal intestinal microbial fermentation and motility, thereby relieving the symptoms of the disease.

3. Description of the Prior Art

Previously, one of the inventors developed and patented a method of "Accelerated Gas Removal From Divers' Tissue Utilizing Gas Metabolizing Bacteria", U.S. Pat. No. 5,630,410. From this research, the inventors developed the concept of adapting the process to medical treatments for the symptoms of diseases or conditions that cause an excess of hydrogen ($H_2$) in the large intestine or bowel.

As stated in Harrison's "Principles of Internal Medicine" Twelfth Edition, Volume I at page 259 (1991), flatulence is a normal occurrence in humans and in animals. In humans, it is often caused by the fermentation in the gut of indigestible polysaccharides and oligosaccharides of food humans eat. Patents such as U.S. Pat. No. 4,376,128 and 5,773,427 sought to defeat flatulence by enzyme treatments either before or after consumption. Others have proposed different combinations of bacteria to re-establish normal gut flora. Chaleil et al. (Ann. Pharm. Fr. 46(2): 133–137, 1988) addressed the subject of a potential link between *Methanobrevibacter smithii* and encephalopathy, and concluded that this link was not present. They were concerned that bismuth salts given to patients as a pharmacological agent could place these patients in jeopardy of encephalopathy if *M. smithii* in the intestinal flora allowed a retention and concentration of bismuth within the patient's brain and other tissues. The work of Chaleil et al. is not relevant to the use of *M. smithii* described by us for the removal of $H_2$ from the intestines of people suffering from Irritable Bowel Syndrome, nor is the instant invention relevant to encephalopathy or bismuth metabolism by *M. smithii*. The only link between this work and that of Chaleil et al. is the coincidental interest in *M. smithii* as a normal constituent of the human intestinal flora. The intent of this prior art is to re-establish normal flora concentration.

Brody (U.S. Pat. No. 5,443,826, 1995) relates to the removal of a significant quantity of the intestinal flora of patients suffering from complications induced by an abnormal, pathogenic flora. Brody then proposes to replace the abnormal flora with cultures of normal flora in their usual relative concentrations, to reestablish intestinal normalcy and promote general patient health. The instant invention differs from that of Brody by adding a significant surplus of only one microbial constituent of the intestinal flora, for example *M. smithii*. The instant goal is not to establish a normal flora, but to establish an exceptional concentration of a single purpose flora for a purpose not anticipated by Brody or any others, namely to remove $H_2$ from the intestines of people suffering from excess intestinal production of $H_2$ and thereby relieve the symptoms. Brody's invention is not relevant to $H_2$ removal, nor does our invention call for the loss of any pathogenic intestinal flora. The only link between our work and that of Brody is the coincidental interest in *M. smithii* as a normal constituent of the human intestinal flora.

With irritable bowel syndrome, some people experience abdominal pains caused by gas trapped in the large intestine. In many cases, a large fraction of this gas is $H_2$, which is generated in the large intestine as an end product of the metabolism by certain species of bacteria. These bacteria are an established part of the intestinal flora of most people, but the amount of $H_2$ they make can vary widely among individuals, and between diets. Many people also harbor microbes that consume this $H_2$ to form several possible end products. The purpose of this invention is to treat the problem of excess intestinal $H_2$ by using a natural approach: by introducing more of the natural intestinal microbes that consume the $H_2$.

In healthy humans with a healthy gut and diverse and nutritionally adequate diet, digestive enzymes in the mouth, stomach, or small intestine break down much of the food ingested, and the digested nutrients are absorbed. The healthy large intestine (colon) houses a large number of microbial species that metabolize the nutrients that are not fully absorbed higher in the digestive tract. Some microbes ferment the complex poly- and oligosaccharides for which humans have no digestive enzymes, for example the cellulose and hemicellulose of plant cell walls, the stachyose in beans and the trehalose in mushrooms. In some individuals, certain digestive enzymes are missing or defective and food products that are absorbed by most people in the small intestine reach the large intestine in unusually large quantities; lactase deficiency leading to colonic lactose fermentation is one example.

A complex community of different species of microbes accomplishes colonic fermentation. The microbes metabolize the material entering the large intestine to a variety of end products including water, acetic, propionic and butyric acids, and the gases $H_2$ and carbon dioxide ($CO_2$). In some individuals and in ruminant animals, methane ($CH_4$) is produced. Microbes that produce methane consume $H_2$ as part of the metabolic pathway. Accumulation of large quantities of $H_2$ in the colon occurs when the $H_2$-producing microbes generate amounts of $H_2$ far in excess of the amounts that can be metabolized by the $H_2$-consuming microbes. Normal mammalian physiological mechanisms cannot remove the excess $H_2$ rapidly enough through flatulence, causing excessive pressure.

Some people harbor large concentrations of a methane-producing organism, *Methanobrevibacter smithii*. It reduces carbon dioxide with $H_2$ to produce methane and water:

$$4H_2 + CO_2 \rightarrow CH_4 + 2H_2O \quad \text{(Eq. 1)}$$

This process uses four volumes of $H_2$ to produce one volume of methane and two volumes of water, and can significantly reduce the gas pressure caused by production of $H_2$ in the colon. About 20% of the colonic gas is absorbed through the intestinal wall, into the bloodstream, and expired in the breath. The rest of the gases exit the body as flatus.

In many people, *Methanobrevibacter smithii* concentrations in the colon are too low to account for significant consumption of $H_2$. Instead of microbial species that produce methane (Eq. 1), these people harbor colonic microbes that use $H_2$ to reduce carbon dioxide to acetic acid ($CH_3COOH$) and water.

$$4H_2 + 2CO_2 \rightarrow CH_3COOH + 2H_2O \quad \text{(Eq. 2)}$$

An example of a microbe that is common in mammalian colons and is capable of such a consumption of $H_2$ is Acetitomaculum spp. About 98% of the acetic and other acids produced in colonic fermentation are absorbed and used by host body tissues as a source of energy or carbon. The rest of the acids exit the body in fecal material.

The painful buildup of $H_2$ gas in the large intestine is caused by such conditions or circumstances as the simultaneous effects of excessive food substrates reaching the intestine, a superabundance of $H_2$-producing bacteria, and inadequate concentrations of $H_2$-consuming microbes in the colonic microbial community. This problem is known in medicine under the general name of irritable bowel syndrome, or spastic colon, and is one of the most frequently occurring gastrointestinal disorders. Various techniques are used to reduce the symptoms. These techniques include modification of diet (to reduce dietary intake of the polysaccharides being malabsorbed), ingestion of charcoal (to absorb some of the gas), and dosing with simethicone (to disperse gas bubbles and prevent formation of large gas pockets). These remedies have variable degrees of success.

Attempts have been made to control "stomach gas" in ruminants with various pills. The literature suggests, among many treatment agents, adding polymers, U.S. Pat. No. 5,494,660, actaplanin factor H, U.S. Pat. No. 4,558,036, or amidinureas, U.S. Pat. No. 4,285,972.

There remains a need for an efficient and safe method to reduce $H_2$ emissions and relieve gastric stress in both humans and animals.

SUMMARY OF THE INVENTION

Accordingly, an object of this invention is to provide a method to increase the rate of removal of gaseous $H_2$ from the intestines of people and animals suffering from an excessive accumulation of $H_2$ in the colon.

Another object of the invention is a method of relieving gastric distress caused by excess hydrogen in the gut.

An additional object of the invention is to encapsulate a form of non-toxic, microbe capable of reducing hydrogen in the gut to a lower volume of end-product that can be metabolized or expelled.

These and additional objects of the invention are accomplished by introducing, collectively or singly, into the large intestine high concentrations of $H_2$ consuming microbes. The introduction of $H_2$ metabolizing microbes into the colons of people suffering from intestinal gas pains is intended to relieve the symptom and is not intended as a treatment of the underlying cause. These microbes will convert some of the $H_2$ to water, methane, acetic acid, or other end products having less volume than hydrogen, thereby decreasing gas pressure and flatus.

The microbes are delivered in a manner that will protect their metabolic activity after oral ingestion and passage through the stomach to a release point further down the gut so that the $H_2$ consuming ability of the microbes will be maintained at the site of excess $H_2$ production in the large intestine. Any one of several means of packaging and delivery, including enteric-coated capsules, are available.

More specifically, this invention relates to the development of microbes or microbial supplements that, when delivered orally to the intestine of people or animals suffering from intestinal gas pains caused by $H_2$, metabolize the $H_2$ to other compounds such as water, methane or acetic acid. In addition, this invention relates to the product that delivers the microbes to the intestine.

Other objects, advantages and novel features will be apparent to those that are familiar with the art upon reading the following detailed description of the invention.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representation in each of the figures is diagrammatic and no attempt is made to indicate actual scales or precise ratios. Proportional relationships are shown as approximations.

DESCRIPTION OF THE PREFERRED EMBODIMENTS

Figure 1:
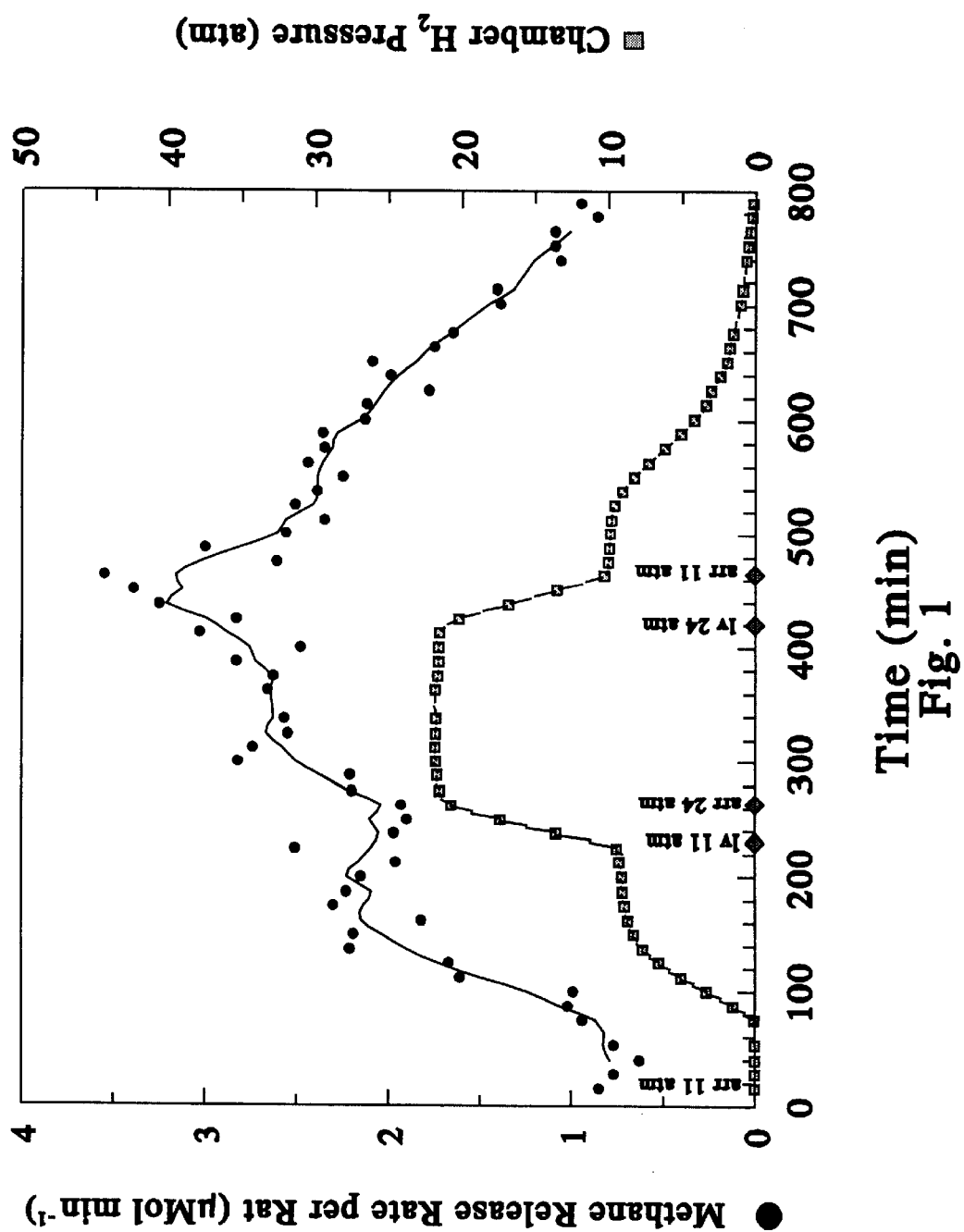
FIG. 1 is a graph of the methane release rate from 5 rats with *Methanobrevibacter smithii* introduced into their intestines. While the rats were breathing a gas mixture that did not contain any $H_2$ (2% $O_2$, balance helium at 11 atm total pressure), they made detectable but small quantities of methane. This was because of a supply of $H_2$ from native bacteria in the intestine that produce $H_2$. The rats then breathed increasing quantities of $H_2$, which were supplied at elevated environmental pressures to drive a significant volume of $H_2$ into the intestine. *Methanobrevibacter smithii* converted increasing amounts of $H_2$ to methane. This demonstrates that *M. smithii* can respond to volumes of $H_2$ in the intestine in great excess of normal physiological values, as in the disease state of irritable bowel syndrome.

This invention relates to the finding that $H_2$ can be removed from the intestines of animals by supplementing their intestinal microbial flora with $H_2$-metabolizing microbes.

In general, any $H_2$-metabolizing microbes that are not toxic and that can be isolated from the intestinal tract of humans or other mammals are useful for this invention. It is impossible to name all microbes meeting these criteria because new species are being isolated almost daily. Preferred microbes are not toxic in an animal's gut and will reduce hydrogen to methane, acetic acid and the like. Illustrative methane-producing microbes (Eq. 1) operable in this invention are *Methanobrevibacter smithii, Methanobre-* vibacter ruminantium, Methanobacterium formicicum, Methanomicrobium mobile, Anaerovibrio lipolytica, and Wolinella succinogenes. The precise identity of the human colonic microbial species responsible for the reduction of carbon dioxide to acetic acid and water (Eq. 2) is not presently known, though there is likely to be more than one organism responsible. Members of the genus Acetitomaculum and the strains CS1Van and CS7H are examples of acetic acid producing microbes isolated from bovine rumens and human feces.

A key objective of the invention is to deliver the microbes in a viable state to the large intestine. Intestinal delivery can be accomplished via anal insertion (for a laboratory animal), but the preferred route is by oral ingestion in the form of a delayed-release capsule.

The preparation of delayed-release capsules that do not dissolve or release contents in the stomach is well known. Such capsules are described in U.S. Pat. Nos. 5,650,170; 5,424,289; 5,417,682; 5,178,866; 4,627,851; 4,904,474; & 5,536,507. Alza Corp., of Palo Alto, Calif. produces enteric coatings in which an enteric-coated outer shell does not dissolve in the acid of the stomach but does dissolve in the mildly alkaline conditions of the intestine. Water permeating through a semipermeable inner capsule causes the capsule to separate, releasing the material packed inside. The time of separation, and therefore location in the transit through the digestive tract, can be precisely controlled by the rate of water imbibition through the semipermeable portion of the capsule. Other patents describing the methods for targeting delivery to the intestine are U.S. Pat. No. 4,079,125; U.S. Pat. No. 4,800,083; U.S. Pat. No. 5,415,864; and U.S. Pat. No. 5,356,625.

The microbes must be capable of returning to active metabolism upon release. The microbes can be included in a slow-release capsule in a number of possible forms; for example, as a freeze-dried product, as a cell paste preparation or in a gel formation. Exact dosages of microbes will vary with the activity of the microbes and the amount of gas per day that needs to be eliminated.

In the preferred embodiment, the person suffering from intestinal $H_2$ takes one or more capsules, tablets, or other form of packaging or non-packaged delivery of the preparation. The preparation contains a calculated dosage of microbes. In the preferred form, the microbes are in a freeze-dried encapsulation. The packaging must pass through the stomach and small intestine unharmed. The packaging begins to dissolve in the small intestine and is fully hydrated and operational on, or shortly after, arrival in the large intestine. This invention demonstrates that live, $H_2$-metabolizing microbes placed in the large intestines of rats do indeed eliminate $H_2$ present in the rats' intestines. Of course, when no longer needed, the microbes die for lack of $H_2$ and are disposed of in normal fecal matter.

Having described the invention, the following examples are given to illustrate specific applications of the invention including the best mode now known to perform the invention. These specific examples are not intended to limit the scope of the invention described in this application.

EXAMPLE 1

Experimental Model for Demonstrating Intestinal $H_2$ Metabolism

Two milliliters of a concentrated culture of Methanobrevibacter smithii in a bicarbonate buffer (with an in vitro activity of 50 μmol $H_2$ uptake per minute) were injected into the caecum (anterior end of the large intestine) of rats, via a cannula introduced from the rectum. The animals (n=5) were then placed in a box. The box was pressurized with 11 atm of a gas mixture containing helium and oxygen (0.2 atm $O_2$), but no $H_2$. A stream of gas passed through the box to a gas chromatograph in order to measure any methane released by the rats. As shown in FIG. 1, significant quantities of methane were detectable. Production of methane could only be caused by metabolism of $H_2$ by M. smithii in the intestines, with endogenous bacteria the only source of the $H_2$. This is assured by finding no methane release from rats that had not been injected with M. smithii, since the strain of rats we were using have no native methane-producing intestinal microbes, but they are known to have native $H_2$-producing bacteria.

To test the capacity of M. smithii to consume more $H_2$ than the amounts generated by the endogenous $H_2$-producing bacteria in these healthy rats, we replaced the helium in the animals' box with $H_2$. Hydrogen was introduced first at a total pressure of 11 atm, and then to a final pressure of 23.7 atm (including 0.2 atm $O_2$). The high pressure of $H_2$ was intended to mimic an extreme disease case. As the rats breathed more $H_2$, the production of methane increased (FIG. 1). This demonstrated that $H_2$ had diffused into the intestine down a partial pressure gradient, and was being consumed by M. smithii. When we subsequently removed the $H_2$ from the animals' box and replaced it with helium again, the release rate of methane fell. Thus we are confident that microbes can be delivered viably to the intestines, and that these microbes can consume far more $H_2$ than the amounts released by the endogenous colonic $H_2$-producing bacteria.

Figure 2:
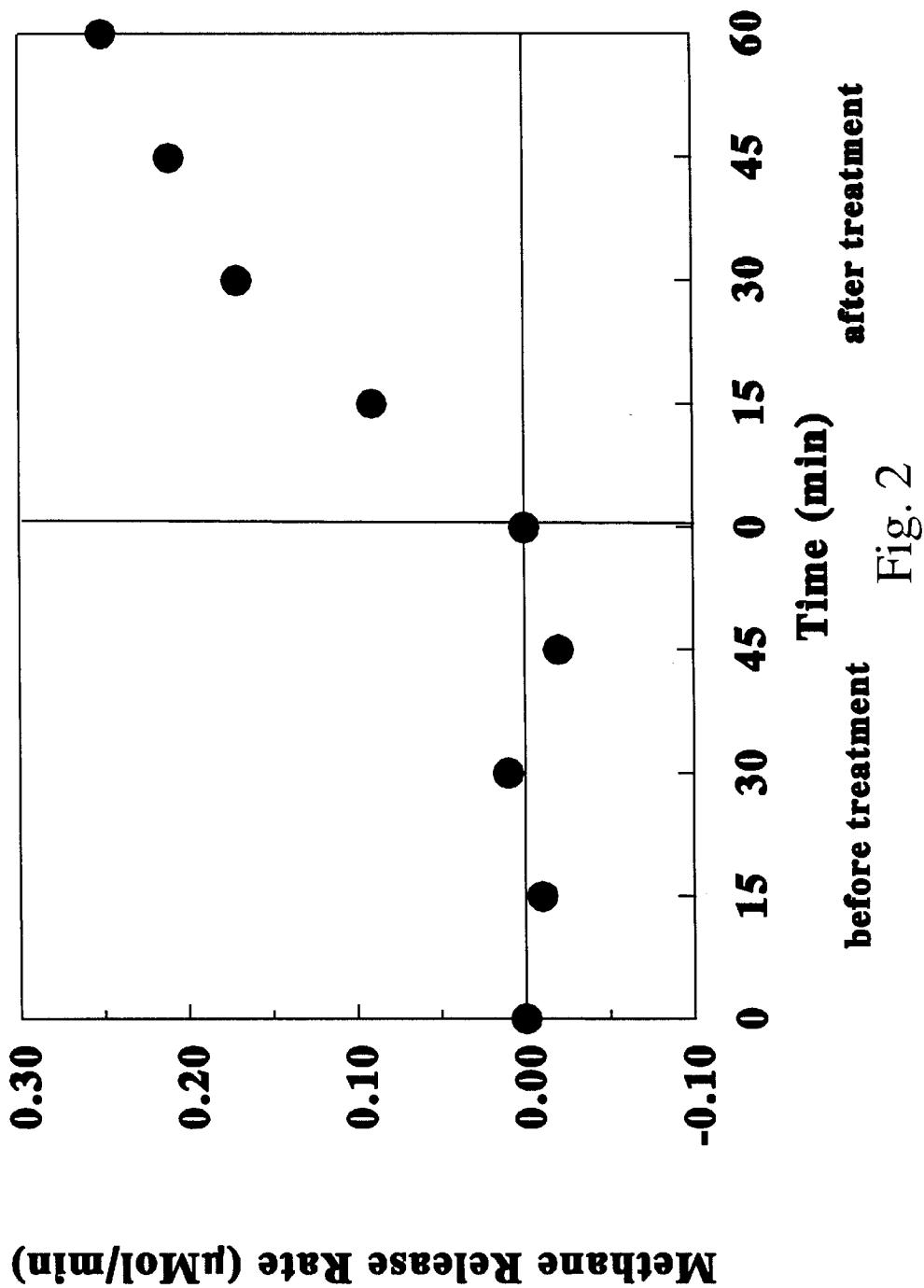
FIG. 2 is a graph of the methane release rate from 4 rats while breathing air at normal atmospheric pressures. Without treatment, rats make undetectable quantities of methane. With *Methanobrevibacter smithii* placed in their large intestines, the rats make significantly more methane. This demonstrates that when these microbes are delivered artificially to the intestine, the microbes can metabolize $H_2$ produced by the native microbial flora of the intestine.

This experiment was successfully completed six more times, with 5 rats per experiment; results were qualitatively similar to those shown in FIG. 1. Animals with M. smithii in their intestines make methane even when no $H_2$ is present in the breathing mixture, because the M. smithii metabolize $H_2$ in the intestine released by endogenous $H_2$-producing bacteria, as illustrated in FIG. 2. Animals with M. smithii make even more methane when $H_2$ is introduced into the breathing mixture, demonstrating that the capacity of these microbes to metabolize $H_2$ extends well beyond the $H_2$ supply rate from endogenous $H_2$-producing bacteria in healthy animals. Animals that did not have M. smithii injected into their intestines do not make detectable methane under these experimental conditions, either with or without $H_2$ in their breathing mixture, because methane-producing bacteria are not native to the intestinal flora of this strain of rats. When lower activities of M. smithii were used than that described above, smaller volumes of methane were released per unit time.

EXAMPLE 2

To confirm that reactions at one atmosphere act the same as reactions under high-pressure conditions, the following test was conducted. Four untreated Sprague-Dawley rats were placed in a box that was ventilated with air. A sample of the air leaving the box was analyzed by gas chromatography for its methane content. No methane beyond the trace (ca. 4 ppm) normally found in air was detected. This is as expected because the Sprague-Dawley strain of rats does not usually have methanogenic organisms native to its intestinal flora. The four rats then had cultures of M. smithii (2 ml volume, 52 μmol $CH_4$/min activity per rat) injected surgically into their caeca. Within minutes, the rate of release of methane became easily detectable and continued to increase over the next hour. This indicated that the cultures of M. smithii were metabolizing $H_2$ produced in the caeca of the rats by native $H_2$-producing bacterial species. Thus, our approach of delivering live *M. smithii* or other methanogenic cultures of microbes to the large intestine in order to convert $H_2$ to $CH_4$ is successful under normal 1 atm conditions.

Obviously, many modifications and variations of the present invention are possible in light of the above teachings. It is therefore to be understood that, within the scope of the appended claims, the invention may be practiced otherwise than as specifically described.

What is claimed is:

1. A method of reducing the symptoms of Irritable Bowel Syndrome, spastic colon, or excessive flatulence or other intestinal distress caused by $H_2$ gas trapped in the intestines, comprising the steps of:
   a. Introducing into the large intestine microbes selected from the groups consisting of $H_2$-consuming microbes;
   b. Permitting said microbes to grow and be maintained in the intestine for a time that is sufficient to eliminate excess accumulation of $H_2$ in the intestine; and
   c. Metabolizing said $H_2$, at normal atmospheric pressure conditions, whereby the rate of elimination of $H_2$ from a person's intestines is accelerated and intestinal distress is relieved, with no serious side, toxic or immunological effects.

2. The method of claim 1, wherein the $H_2$-consuming microbes are delivered orally and pass through an individual's stomach and into said small or large intestine before being released.

3. The method of claim 1, wherein said microbes are selected from the group consisting of microbes that consume $H_2$ and produce methane and microbes that consume $H_2$ and produce acetic acid.

4. The method of claim 3, wherein said microbes are enclosed in a package comprising an enteric coated, slow release container.

5. The method of claim 4, wherein the cause of said intestinal distress is selected from the group of conditions consisting of Irritable Bowel Syndrome, Spastic colon, and excessive flatulence.

6. The method of claim 5, wherein said $H_2$ consuming and methane producing microbes are *Methanobrevibacter smithii*.

7. The method of claim 5, wherein said $H_2$ consuming and acetic acid producing microbes are Acetitomaculum spp.

* * * * *